United States Patent [19]

Bradley et al.

[11] Patent Number: 5,281,578

[45] Date of Patent: Jan. 25, 1994

[54] GALLIUM COMPOUNDS

[75] Inventors: Fontaine C. Bradley, Byfield, Mass.; Danielle T. Frost, Philadelphia; Christen M. Giandomenico, West Chester, both of Pa.

[73] Assignee: Johnson Matthey Public Limited Company, London, England

[21] Appl. No.: 885,687

[22] Filed: May 19, 1992

[51] Int. Cl.$^5$ .................. A61K 37/14; A61K 31/28; C07F 5/00
[52] U.S. Cl. ........................................ 514/6; 514/492; 556/1; 556/32
[58] Field of Search .................. 556/1, 32; 514/6, 492

[56] References Cited

U.S. PATENT DOCUMENTS 2,778,843 1/1957 Brown et al. .................. 260/429.1

OTHER PUBLICATIONS

Canadian Journal of Chemistry, vol. 59, pp. 94-99 (1981).
Chong et al., Canadian Journal of Chemistry, vol. 59, No. 1, 94-99 (Jan. 1981).

*Primary Examiner*—José Dees
*Assistant Examiner*—Porfirio Nazario
*Attorney, Agent, or Firm*—Cushman, Darby & Cushman

[57] ABSTRACT

Gallium(III) complexes of general formula I,

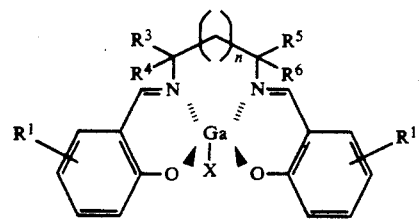

in which $X = O_2CR^2$, halogen, $NO_3$ or $-OA$, $R^1 = H$, alkyl, alkoxy, halogen, $NO_2$ or amino, $R^2 =$ alkyl, alkoxy or aryl, each of $R^3$, $R^4$, $R^5$ and $R^6 = H$ or alkyl and $n = 0$, 1 or 2, or when $n = 0$ and $R^3$ and $R^6$ both $= H$, then $R^4$ and $R^5$ together may form tetramethylene, and $A =$ an identical gallium complex moiety to that to which the oxygen atom is linked, are well absorbed orally, and are indicated as medicaments for hypercalcemia and for cancer chemotherapy.

11 Claims, No Drawings

GALLIUM COMPOUNDS

This invention concerns gallium compounds. More especially it concerns gallium compounds having increased absorption when administered by the oral route.

Salts of the group 13 metal gallium have been known for some time to have anti-tumour activity. More recently, gallium has been shown to reduce serum calcium in patients with hypercalcemia of malignancy. Gallium exerts this latter effect by inhibiting the resorption of calcium from bone; it also increases bone strength so that gallium would also be useful for treating bone disorders associated with accelerated bone loss and decreased bone strength, (see e.g., U.S. Pat. No. 4,704,277 and U.S. Pat. No. 4,529,593 the teaching of which is incorporated herein by reference).

In practice, gallium therapy for hypercalcemia has been difficult to provide. It has been reported that renal toxicity is dose-limiting when gallium is administered as an iv bolus. A seven day continuous iv infusion of gallium showed no renal toxicity for the treatment of cancer-associated hypercalcemia, and while this therapy is effective, it is cumbersome. In order to make gallium therapy more conveniently administered for both cancer chemotherapy and the hypercalcemia of malignancy, and in order to provide wider application of gallium therapy to appropriate bone diseases, an oral dose form of gallium is highly desirable.

Drug absorption from the gastro-intestinal tract occurs at pH 4.5-7. In this pH range the gallium(III) aquoion is extensively hydrolysed to insoluble hydroxides and is very poorly absorbed. Daily oral doses of 400 mg $GaCl_3$ in lung cancer patients yielded mean serum gallium concentrations of 371±142 ug/ml. However, gallium in an appropriate co-ordination environment is stable to hydrolysis in aqueous environment, at pH which is relevant biologically.

The present invention provides novel pharmaceutical compositions comprising an active component which is a gallium complex as defined by formula I hereinafter, and methods of administering gallium to a patient comprising the use of said complexes and the invention has many other inventive and useful aspects.

In particular, the active components according to the invention are gallium(III) complexes of formula I,

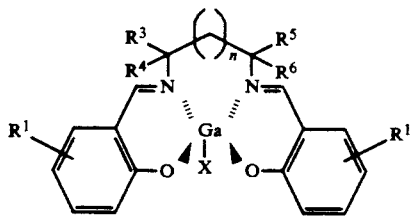

in which,
X=$O_2CR^2$, halogen, $NO_3$ or —O—A,
$R^1$=H, alkyl, alkoxy, halogen, $NO_2$ or amino,
$R^2$=alkyl, alkoxy or aryl,
each of $R^3$, $R^4$, $R^5$ and $R^6$=H or alkyl and
n=0, 1 or 2, or
when n=0, and $R^3$ and $R^6$ both=H, then $R^4$ and $R^5$ together may form tetramethylene, and
A=an identical gallium complex moiety to that to which the oxygen atom is linked.

For ease of reference hereafter, compounds in which X=—O—A will be called "dimers".

The invention further provides a process for the production of compounds of formula I, comprising reacting a tetradentate Schiff base of general formula II,

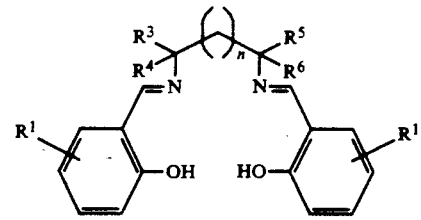

wherein $R^1$-$R^6$, and n are as defined above, with a gallium(III) compound, a) which is gallium(III) hydroxide to form a dimer compound of formula I in which X=—O—A, and when a compound of formula I in which X=$O_2CR_2$ is desired, reacting said dimer with an acylating agent, especially an acid of formula $R^2COOH$, or b) which is gallium(III) halide or nitrate, to form the corresponding compound of formula I in which X is halogen or nitrate.

The dimer compounds thus serve two functions, as active compounds according to the invention, and as intermediates for those compounds of formula I in which X=$O_2CR_2$.

Where substituents $R^1$ to $R^6$ are alkyl or alkoxy, they preferably have from 1 to 6 carbon atoms, more preferably from 1 to 4 carbon atoms.

Where substituent $R^1$ is amino, it is preferably dialkylamino, in which each alkyl has from 1 to 6 carbon atoms.

Preferred compounds of formula I are those in which $R^3$ and $R^4$ are H and n is 0. Preferably, when X is halogen, it is chlorine.

The compound of formula I in which $R^1$ and $R^3$ to $R^6$ are hydrogen, and X is chlorine, has been reported in the academic literature. (Can J Chem, 59, 94, 1980). No utility is suggested for this compound, and it could not be expected that it would exhibit high oral absorption according to the tests described hereinafter. The remaining compounds of formula I are believed to be novel.

In the preparation of the compounds of formula I, the starting materials are known and may be prepared according to known methods, or may be purchased from specialist laboratory chemical suppliers. The gallium-containing starting materials are suitably salts such as $GaCl_3$, $Ga(NO_3)_3$ or freshly precipitated $Ga(OH)_3$. The tetradentate Schiff base is prepared by condensation of a primary diamine with two equivalents of a 2-hydroxybenzaldehyde, in alcohol.

The reaction of the Schiff base with the gallium compound is suitably carried out in a solvent such as an alcoholic medium, boiling ethanol is preferred for many compound preparations. The process is more particularly described in specific compound preparations described in the Examples hereinafter. It will readily be appreciated that it may be desirable to use a salt form of the Schiff base, or to carry out the reaction in the presence of a base, as exemplified in the preparation of compounds of formula I in which X is chlorine or nitrate respectively. The product complexes may be isolated and purified using conventional techniques.

The complexes of the invention provide good oral absorption of gallium compared to commercially-available preparations which are currently used to treat cancer-related hypercalcemia, when assessed by in vivo tests in rats, as described hereinafter. The complexes of the invention are also indicated for the treatment of excessive loss of calcium from bone tissue and for inhibiting bone resorption, and are therefore indicated for the treatment of a patient having an excessive calcium loss and bone resorption disorder.

The active complexes according to the present inventions may be administered to a patient in the form of pharmaceutical compositions formulated according to well known principles. Thus, the composition comprises the active ingredient, preferably in a unit dose, in admixture with a pharmaceutically acceptable diluent or carrier. The active complexes of the invention are assessed to have particular activity when taken orally, and therefore, preferred compositions are those formulated in the form of capsules, tablets, dragees or other solid compositions, or as a solution or suspension, for example, as a syrup, for oral administration. Suitable pharmaceutically acceptable diluents and carriers, and other components, including colouring and flavouring agents, and methods for formulation, are generally known.

Although the active complexes of the invention have particular utility for oral administration, the invention is not to be regarded as limited to methods of treatment and compositions solely for oral administration. Thus, compositions for injections, suppositories, sustained release forms of such or for implantation and the like, may be formulated in conventional manner, and may provide advantages for particular courses of treatment or for combined therapy.

Dosage rates may suitably lie in the range of 0.1 to 100 mg/kg body weight. Preferably, the dosage is sufficient to maintain a level of 1 to 1.5 µg gallium per ml of blood, and the dose may suitably be in the range 0.5 to 1.5 g of gallium compound per day. Such a dose may be administered as a single unit dose or in a number of smaller unit doses. Other active compounds may be administered separately or together with the gallium complex, or supplemental therapy may be included in a course of treatment for a patient.

As representatives of compounds of the invention, the following compounds of formula I may be mentioned:

| ($R_3$ = H) | | | | | | |
|---|---|---|---|---|---|---|
| $R^1$ | $R^4$ | $R^5$ | $R^6$ | X | n | Preparative Example |
| H | H | H | H | O-Gasalen | 0 | 1 |
| H | H | H | H | Cl | 0 | 2 |
| H | H | H | H | $NO_3$ | 0 | 3 |
| H | H | H | H | OAc | 0 | 4 |
| H | H | H | H | $O_2CEt$ | 0 | 5 |
| H | H | H | H | $O_2CC_7H_{15}$ | 0 | 6 |
| H | H | H | H | $O_2CC_6H_5$ | 0 | 7 |
| 3-OMe | H | H | H | OAc | 0 | 8 |
| 5-Cl | H | H | H | OAc | 0 | 9 |
| 5-Me | H | H | H | OAc | 0 | 10 |
| H | Me | H | H | OAc | 0 | 11 |
| H | —$(CH_2)_4$— | | H | OAc | 0 | 12 |
| 4-$NMe_2$ | H | H | H | OAc | 0 | 13 |
| 5-OMe | H | H | H | OAc | 0 | 14 |
| H | H | Me | Me | OAc | 0 | 15 |
| H | H | H | H | OAc | 1 | 16 |

The invention will now be described in the following examples, which illustrate but are not intended to limit the scope of the invention.

EXAMPLES

A typical preparation of freshly precipitated Ga(OH)$_3$ used in the following examples is as follows:

20 ml 1.1M aqueous $GaCl_3$ was hydrolysed with aqueous NaOH to a final pH of 8.35 and a final volume of 100 ml. The suspension was centrifuged at 5000 rpm for 10 minutes, the supernatant liquor was decanted and the Ga(OH)$_3$ resuspended in deionised water three times. The Ga(OH)$_3$ was washed once more in this manner with absolute ethanol and finally resuspended in absolute ethanol for use in preparation of the complexes.

In a typical preparation of the Schiff base tetradentate ligand, two equivalents of aldehyde in methanol was added slowly to one equivalent of diamine in methanol. In most instances a crystalline solid precipitated and was used without further purification.

In a typical preparation of a gallium complex where X of formula I is carboxylate, a suspension of Ga(OH)$_3$ in ethanol was added to a boiling solution of the tetradentate Schiff base in ethanol and boiled for approximately half an hour. The suspension was then cooled, filtered through celite and stripped of solvent to yield, in most instances, a mixture of compounds as a yellow solid. The yellow solid was then dissolved in methanol and stirred with excess carboxylic acid. Concentration of the solution often caused precipitation of analytcially pure LGaO$_2$CR (L=tetradentate Schiff base).

Abbreviations

SalenH$_2$; N,N'-ethylenebis(salicylideneamine);
3-MeOsalenH$_2$; N,N'-ethylenebis(3-methoxysalicylideneamine);
5-ClsalenH$_2$; N,N'-ethylenebis(5-chlorosalicylideneamine);
5-MesalenH$_2$; N,N'-ethylenebis(5-methylsalicylideneamine);
Sal-1,2-pnH$_2$; N,N', 1,2-propylenebis(salicylideneamine);
SalachH$_2$; N,N', trans-1,2-cyclohexanebis(salicylideneamine);
SalmpnH$_2$; N,N'-1,2-diamine-2-methylpropanebis(salicylidene amine);
Sal-1,3-pnH$_2$; N,N'-1,3-propylenebis(salicylideneamine;
4-Me$_2$NsalenH$_2$; N,N'-ethylenebis(4-N,N-dimethylaminesalicylideneamine);
5-MeOsalenH$_2$; N,N'-ethylenebis(5-methoxysalicylideneamine)

EXAMPLE 1

(Gasalen)$_2$O

A 100 ml suspension of Ga(OH)$_3$ in ethanol prepared from 20 ml 1.1M GaCl$_3$, was added to a hot suspension of 4 g salenH$_2$ in 100 ml ethanol and heated at boiling point for about 15 minutes. The bright yellow suspension was cooled, filtered through diatomaceous earth and the filtrate stripped of solvent to leave 3.5 g of solid. 1.5 g yellow solid was recrystallised from 20 ml hot DMSO, washed with diethyl ether and dried.

| Analysis for $C_{32}H_{28}N_4O_5Ga_2 \cdot H_2O$ | | | | |
|---|---|---|---|---|
| | % C | % H | % N | % Ga |
| Calc: | 54.44 | 4.28 | 7.94 | 19.75 |
| Found | 54.25 | 4.33 | 7.94 | 19.40 |

EXAMPLE 2

GasalenCl

This compound was prepared from 2 g salen according to a published procedure with slight modifications (K S Chong et al, Can J Chem, 59, 94, 1980). The crude product was only slightly soluble in the reaction solvent THF, and benzene extraction according to the published procedure was inefficient. Thus the THF insoluble residue from the reaction was stirred briefly in water to remove NaCl, filtered and dried under vacuum. This material was then extracted with boiling acetone, gravity filtered hot and the solvent volume reduced with gentle boiling.

Crystallisation was allowed to proceed first at room temperature and then at 0° C. The crystalline solid was filtered and dried to yield 0.6 g.

| Analysis for $C_{16}H_{14}N_2O_2GaCl$ | | | |
|---|---|---|---|
| | % C | % H | % N |
| Calc: | 51.73 | 3.80 | 7.54 |
| Found | 51.67 | 3.84 | 7.56 |

EXAMPLE 3

GasalenNO₃

To a stirred hot solution of 1.26 g H₂salen and 0.3 g LiOH in 60 ml methanol was added a suspension of 2 g $(Ga(NO_3)_3 \cdot 9H_2O$ in 60 ml methanol. The mixture was heated for a few minutes. The clear, pale yellow solution was concentrated to about 50 ml and chilled to −20° C. for 16 hours. Precipitated LiNO₃ was filtered off, the filtrate was concentrated to about 25 ml and about 40 ml acetone was added. The mixture was chilled to −20° C. for 2 hours. A pale yellow solid was filtered off and the volume of filtrate was reduced. A crystalline solid formed in the viscous yellow solution. This was filtered off, carefully washed with small volumes of very cold (T<0° C.) methanol, then with room temperature acetone, before being vacuum dried to leave 0.92 g pale yellow solid.

| Analysis for $C_{16}H_{14}N_3O_5Ga \cdot 2H_2O$ | | | |
|---|---|---|---|
| | % C | % H | % N |
| Calc: | 44.27 | 4.18 | 9.68 |
| Found | 44.12 | 4.37 | 9.42 |

EXAMPLE 4

GasalenOAc 2.93 g (salenGa)₂O (Example 1) was stirred in 150 ml methanol and 20 ml glacial acetic acid for 5 minutes. The volume was reduced by about 50% on the "rotovap" and the product precipitated. The mixture was allowed to stand for 3 hours at 20° C., the yellow solid filtered, washed with acetone and ether and dried to yield 2 g yellow solid.

| Analysis for $C_{18}H_{17}N_2O_4Ga$ | | | |
|---|---|---|---|
| | % C | % H | % N |
| Calc: | 54.72 | 4.34 | 7.09 |
| Found | 54.73 | 4.37 | 7.11 |

EXAMPLE 3

GasalenO₂CEt

This was prepared by a procedure similar to Example 4 from 2 g (Gasalen)₂O and 4 ml propionic acid in 150 ml MeOH. After addition of propionic acid the solvent was removed under vacuum and the resulting yellow oil recrystallised from 20 ml acetone by adding hexane to the cloud point (70 ml) and allowing crystallisation to proceed, 1.36 g.

| Analysis for $C_{19}H_{19}N_2O_4Ga \cdot \frac{1}{4}H_2O$ | | | |
|---|---|---|---|
| | % C | % H | % N |
| Calc: | 55.18 | 4.75 | 6.77 |
| Found | 55.25 | 4.47 | 6.70 |

EXAMPLE 6

Gasalenoctanoate

This compound was made from 2 g (Gasalen)₂O (Example 1) and 1.83 ml octanoic acid in 75 ml methanol. Precipitation was induced by adding ether to yield 1.7 g of fluffy off-white solid.

| Analysis for | | | |
|---|---|---|---|
| | % C | % H | % N |
| Calc: | 60.15 | 6.10 | 5.85 |
| Found | 60.16 | 6.10 | 5.83 |

EXAMPLE 7

Gasalenbenzoate

This compound was prepared from 0.50 g (Gasalen)₂O (Example 1) and 0.18 g benzoic acid in 50 ml methanol. After stirring the reaction mixture for 3 hours, 0.27 g yellow solid was filtered off, washed with ether and dried.

| Analysis for $C_{23}H_{19}N_2O_4Ga$ | | | |
|---|---|---|---|
| | % C | % H | % N |
| Calc: | 60.43 | 4.19 | 6.13 |
| Found | 60.41 | 4.01 | 6.04 |

EXAMPLE 8

3-MeOsalenGaOAc

3-MeOsalenH₂ was prepared from 5 g o-vanillin in 50 ml absolute ethanol and 1 g ethylenediamine in 50 ml absolute ethanol. 5 g of yellow-orange crystalline solid formed which was filtered, washed with ethanol and dried.

Ga(OH)₃ in 100 ml ethanol, from 8.3 ml 1.1M aqueous GaCl₃, was boiled for about 1 hour in a solution of 2 g 3-MeOsalen in 100 ml ethanol, to yield 2.4 g bright yellow solid.

To 1.8 g of this solid, stirred as a suspension in 250 ml methanol, was added 5.3 ml glacial acetic acid. The clear, bright yellow solution was reduced in volume on the "rotovap" to about 60 ml during which a yellow solid formed. This was allowed to stand at −20° C. for 1 hour, the solid filtered, washed and dried to yield 1.4 g yellow solid.

| Analysis for $C_{20}H_{21}N_2O_6Ga.1\frac{1}{2}H_2O$ | | | |
|---|---|---|---|
| | % C | % H | % N |
| Calc: | 49.82 | 5.02 | 5.68 |
| Found | 49.69 | 4.94 | 5.68 |

EXAMPLE 9

Ga5-chlorosalen 5-chlorosalenH$_2$ was prepared from 14 g 5-chlorosalicylaldehyde and 3 ml ethylene-diamine in a total of 150 ml methanol. The product precipitated without reducing the volume, with a yield of 13 g.

A 120 ml ethanol suspension of Ga(OH)$_3$ from 21.3 ml 0.84M aqueous GaCl$_3$ was added to a solution of 4 g 5-chlorosalen in 700 ml ethanol at boiling point. The suspension was boiled for half an hour, left to cool and centrifuged at 9000 rpm for 10 minutes. The supernatant liquor was decanted and stripped of solvent to leave 3 g of pale yellow solid. 1 g of this solid was dissolved in 200 ml absolute ethanol and 2.8 ml glacial acetic acid was added. After precipitation was complete, the pale yellow powder was filtered, washed and dried to yield 560 mg.

| Analysis for $C_{18}H_{15}N_2O_4Cl_2Ga$ | | | |
|---|---|---|---|
| | % C | % H | % N |
| Calc: | 46.60 | 3.26 | 6.04 |
| Found | 46.88 | 3.81 | 5.75 |

EXAMPLE 10

Ga5-methylsalenOAc 5-methylsalicylaldehyde was prepared from p-cresol by the Duff reaction. The Schiff base (5-Mesalen) was prepared in 100 ml methanol from 1.2 ml ethylenediamine and 5.03 g 5-methylsalicylaldehyde to yield 2.75 g product.

Ga(OH)$_3$, prepared from 12 ml 0.84M GaCl$_3$ in ethanol was added to a solution of 2 g 5-methylsalen in 400 ml boiling ethanol. The suspension was boiled for half an hour, allowed to cool, filtered through celite and stripped of solvent under vacuum. The yellow solid was dissolved in 300 ml methanol and 3 ml glacial acetic acid was added. After stirring for 1½ hours the solution was stripped to dryness and the yellow solid recrystallised from acetone. The crystalline material contained acetone not removed under vacuum. The solid was recrystallised from ethylacetate to yield 1.16 g yellow solid.

| Analysis for $C_{20}H_{21}N_2O_4Ga$ | | | |
|---|---|---|---|
| | % C | % H | % N |
| Calc: | 56.77 | 5.00 | 6.62 |
| Found | 56.74 | 4.99 | 6.55 |

EXAMPLE 11

Ga(Sal-1,2-pn)OAc

Sal-1,2-pnH$_2$ was made from 3 ml±1,2-propanediamine and 7.54 ml salicylaldehyde in 130 ml methanol as a yellow oil, yielding 9.7 g. 4 g Sal-1,2-pnH$_2$ was allowed to react with Ga(OH)$_3$ from 6.39 ml 0.84M GaCl$_3$m, in 250 ml boiling methanol for half an hour. The mixture was allowed to cool, filtered through celite and stripped of solvent to leave 5.61 g yellow solid. A solution of 5.5 g of the yellow solid in 100 ml MeOH, was stirred with 9 ml glacial acetic acid for 1 hour and stripped of solvent to leave a yellow oil which solidified on standing. This was recrystallised from 250 ml hot acetone to yield 1.2 g pale yellow solid.

| Analysis for $C_{19}H_{19}N_2O_4Ga$ | | | | |
|---|---|---|---|---|
| | % C | % H | % N | % Ga |
| Calc: | 55.78 | 4.68 | 6.85 | 17.04 |
| Found | 55.81 | 4.63 | 6.85 | 16.48 |

EXAMPLE 12

GasaldachOAc

To a stirred solution of 3 g trans-1,2-diaminocyclohexane in 75 ml methanol was added slowly 6.41 g salicylaldehyde in 25 ml methanol. SaldachH$_2$, obtained as 7.23 g yellow granular product, was filtered, washed and dried.

A methanol suspension of Ga(OH)$_3$ from 16.6 ml 0.84M GaCl$_3$ was added to 3 g saldachH$_2$ in 200 ml boiling absolute ethanol. The suspension was boiled for half an hour and filtered through celite. Little material was extracted into the ethanol. The celite was extracted with CH$_2$Cl$_2$ and the solvent evaporated from the extract under vacuum to leave 3.31 g yellow solid.

0.5 g of this yellow solid was dissolved in 400 ml 50:50 CH$_2$Cl$_2$/MeOH and about 1 ml glacial acetic acid was added. After 3 hours, the volume of the mixture was reduced to 75 ml and then chilled to −20° C. 0.49 g of white solid was filtered off, washed with ether and dried.

| Analysis for $C_{22}H_{23}N_2O_4Ga.H_2O$ | | | |
|---|---|---|---|
| | % C | % H | % N |
| Calc: | 56.56 | 5.39 | 6.00 |
| Found | 56.74 | 5.68 | 5.79 |

EXAMPLE 13

4-Me$_2$NsalenGaOAc

4-N,N-dimethylaminosalicylaldehyde was prepared according to a published procedure (Baird and Shriner, J Am Chem Soc 1964, 68, 3142).

4-Me$_2$NsalenH$_2$ was prepared from the reaction of ethylenediamine with two equivalents of 4-N,N-dimethylaminosalicylaldehyde in methanol. The product was filtered from the reaction mixture after standing at −20° C. overnight and used as is.

Ga(OH)$_3$ in about 40 ml ethanol, from 10.1 ml 0.84 M aqueous GaCl$_3$, was boiled for about ½ hour in a solution of 2 g 4-Me$_2$NsalenH$_2$ in 250 ml ethanol. During the reaction, solvent boiled away to leave a volume of 75 ml. When the reaction mixture cooled to room temperature a solid formed. This solid product was removed by filtration and washed with ether to leave 1.25 g fluffy solid. This solid was dissolved in 150 ml methanol, filtered and the filtrate allowed to react with acetic acid. Reduction of solvent volume caused a precipitate to form which was filtered, washed with ether and dried to yield two crops of crystalline solid with a combined weight of 0.9 g.

| Analysis for $C_{22}H_{27}N_4Ga$ | | | |
|---|---|---|---|
| | % C | % H | % N |
| Calc. | 54.91 | 5.66 | 11.64 |
| Found | 54.96 | 5.64 | 11.64 |

EXAMPLE 14

5-MeOsalenGaOAc

5-MeOsalenH$_2$ was prepared in the same manner as the free ligand in Example 8.

A suspension of Ga(OH)$_3$ in 50 ml ethanol, from 13.5 ml 0.84 M aqueous GaCl$_3$, was boiled with a solution of 3 g 5-MeOsalenH$_2$ in 400 ml absolute ethanol for ½ hour to yield 3.3 g yellow solid. The solid was stirred with two equivalents acetic acid in methanol and stripped of solvent to leave a solid. The solid was recrystallised from methanol/toluene.

| Analysis for $C_{20}H_{21}N_2O_6Ga$ | | | |
|---|---|---|---|
| | % C | % H | % N |
| Calc. | 52.78 | 4.65 | 6.16 |
| Found | 52.83 | 4.71 | 5.96 |

EXAMPLE 15

SalmpnGaOAc

SalmpnH$_2$ was synthesised from 2 g 1,2-diamino-2-methylpropane and 5.54 g salicylaldehyde in 100 ml methanol. The solvent volume was reduced by evaporation and 4 g yellow solid product was filtered off, washed with hexane and dried.

A suspension of Ga(OH)$_3$ in 50 ml absolute ethanol, from 18.1 ml 0.84 M aqueous GaCl$_3$, was boiled with a solution of 3 g SalmpnH$_2$ and 200 ml boiling absolute ethanol, centrifuged and stripped of solvent to leave 3.9 g yellow solid. The solid was stirred in methanol with two equivalents of acetic acid and the reaction mixture stripped to dryness to leave a yellow solid product which was recrystallised from 1:1 acetone/hexane.

| Analysis for $C_{20}H_{21}N_2O_4Ga$ | | | |
|---|---|---|---|
| | % C | % H | % N |
| Calc. | 56.77 | 5.00 | 6.62 |
| Found | 56.76 | 5.05 | 6.64 |

EXAMPLE 16

Sal-1,3-pnGaOAc

Sal-1,3-pnH$_2$ was prepared in 61% yield from 1,3-diaminopropane and two equivalents of salicylaldehyde in 300 ml methanol to yield 18 g 61% yellow solid. This product was used as is.

A suspension of Ga(OH)$_3$ in 50 ml ethanol, from 10.6 ml 0.84M aqueous GaCl$_3$ was boiled with 2.5 g Sal-1,3-pn in 200 ml absolute ethanol for ½ hour. The mixture was stripped of solvent and the residue taken up in CH$_2$Cl$_2$. This suspension was centrifuged, the supernate filtered through celite and the filtrate stripped of CH$_2$Cl$_2$ to leave 2 g yellow solid.

0.74 g of this solid was stirred with two equivalents acetic acid, stripped of solvent and the yellow mass triturated with ether to leave a yellow solid.

| Analysis for $C_{19}H_{19}N_2O_4Ga$ | | | |
|---|---|---|---|
| | % C | % H | % N |
| Calc. | 55.78 | 4.68 | 6.85 |
| Found | 55.61 | 4.80 | 6.88 |

According to the invention, compounds were tested for oral absorption in rats. Male Sprague Dawley rats weighing 150–225 g were purchased from Harlan Sprague Dawley, Inc., (Indianapolis, Ind.). The gallium standard solution is from Aldrich Chemical Co. (Milwaukee, Wis.). Metofane is a product from Pitman-Moore (Mundelein, Ill.), and all other Chemicals are commercially available. Gallium test compounds were dissolved in 18 megaohm water (Millipore, Bedford, Mass.) or suspended in 0.5% carboxymethyl cellulose in 5% ethanol, if the compound was not water soluble. The suspensions were sonicated at room temperature for about 5 minutes.

For stomach and intestine administrations, rats were anaesthetised with metofane, and a one-inch incision made to expose the stomach and a portion of the small intestine. A ligation was made immediately below the pylorus, and a second ligation was made 1 cm below to assure no leakage. For oral gavage administrations, 18-gauge ball-tipped animal feeding needles (Popper & Sons, Inc, New Hyde Park, N.J.) were used. For stomach injections, needles were inserted in the middle of the pyloric part of the stomach which has an opaque thick muscular wall, and intestinal injections were made about 0.5 cm below the second ligation with the needle pointed down and away from the stomach.

Sutures were made with 3-4 stitches with 3-0 silk surgical thread (Ethicon Inc, Somerville, N.J.). The tail vein was used for intravenous injections. With the exception of oral gavage administrations, all injections were made with 30-gauge needles to minimise the possibility of leakage. The dose was 0.067 mmol/kg. Approximately 300 μl blood samples were collected at 0.17, 0.5, 1.0, 2.0, 4.0 hours following compound administration. The blood was placed in 1 ml Eppendorf tubes pre-coated with 50 μl heparin (1000 U/ml and air dried, so there was no blood dilution involved. The plasma was recovered after the blood was centrifuged for 2 minutes in a Fischer Micro-centrifuge, Model 235B, and its gallium content measured by a Varian Flameless Atomic Absorption Spectrometer. The standard curve was linear in the gallium concentrations of 5–100 ng/ml. The area under the concentration (AUC) versus time curve for 0–4 hours was estimated.

| Four-Hour Area Under Curve | | |
|---|---|---|
| Compound | Example | 4h-AUC (ng/ml)h |
| GasalenCl | 2 | 15852 |
| (Gasalen)$_2$O | 1 | 14942 |
| GasalenOAc | 4 | 10000 |
| Ga(NO$_3$)$_3$ | prior art | 897 |

| Four-Hour Area Under Curve | | |
|---|---|---|
| Compound | Example | 4h-AUC (ng/ml)h |
| compound | | |

The 4-hour AUC's indicate that good oral absorption of gallium occurs from the intestine and that appropriate formulation of the gallium compounds of formula I will yield a convenient dose form of gallium for the treatment of cancer, the hypercalcemia of malignancy and other diseases characterised by excessive bone loss and bone weakening. The difference in the above tests between the prior art compound gallium nitrate, and the compounds of formula I, is extremely marked.

We claim:

1. A pharmaceutical composition comprising a gallium(III) complex of formula I,

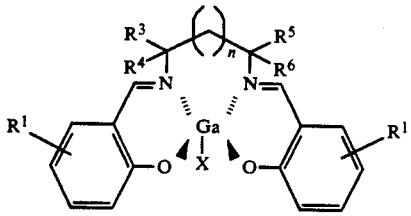

in which,
X=$O_2CR^2$, halogen, $NO_3$ or —O—A,
$R^1$=H, alkyl, alkoxy, halogen, $NO_2$ or amino,
$R^2$=alkyl, alkoxy or aryl,
each of $R^3$, $R^4$, $R^5$ and $R^6$=H or alkyl and
n=0, 1 or 2, or
when n=0, and $R^3$ and $R^6$ both=H, then $R^4$ and $R^5$ together may form tetramethylene, and
A=an identical gallium complex moeity to that to which the oxygen atom is linked, in admixture with a pharmaceutically acceptable diluent or carrier.

2. A composition as claimed in claim 1, wherein in the complex of formula I, $R^3$ is hydrogen.

3. A composition as claimed in claim 2, wherein in the complex of formula I, $R^6$ is hydrogen and n is 0.

4. A composition as claimed in claim 1, wherein the gallium complex is selected from GasalenCl, (Gasalen)$_2$O and GasalenOAc.

5. A composition as claimed in claim 1 in tablet, capsule, syrup or suspension form suitable for oral administration.

6. A gallium(III) complex of formula I,

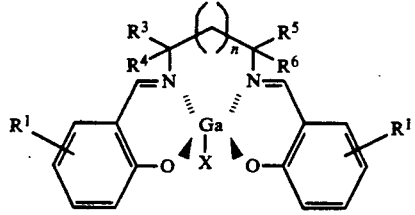

in which,
X=$O_2CR^2$, halogen, $NO_3$ or —O—A,
$R^1$=H, alkyl, alkoxy, halogen, $NO_2$ or amino,
$R^2$=alkyl, alkoxy or aryl,
each of $R^3$, $R^4$, $R^5$ and $R^6$=H or alkyl and
n=0, 1 or 2, or
when n=0, and $R^3$ and $R^6$ both=H, then $R^4$ and $R^5$ together may form tetramethylene, and
A=an identical gallium complex moeity to that to which the oxygen atom is linked,
provided that when $R^1$ and $R^3$ to $R^6$ are hydrogen, X is not chlorine.

7. A complex as claimed in claim 6, wherein $R^3$ is hydrogen.

8. A complex as claimed in claim 7, wherein $R^6$ is hydrogen and n is 0.

9. A complex as claimed in claim 6, wherein X is chlorine.

10. A complex as claimed in claim 6, wherein X is —O—A.

11. In a method involving treatment with a gallium compound for at least one of excessive calcium loss and bone resorption disorders wherein said compound is administered to a patient in need of such treatment, the improvement which comprises utilizing as said gallium compound, a compound according to claim 1.

* * * * *